United States Patent
Chang et al.

[11] Patent Number: 6,062,084
[45] Date of Patent: May 16, 2000

[54] APPARATUS FOR DETECTING WAFER EDGE DEFECTS AND METHOD OF USING

[75] Inventors: Chi-Wei Chang, Hsin-Chu; Chung-Yi Lee, Chupei, both of Taiwan

[73] Assignee: Taiwan Semiconductor Manufacturing Co., Ltd., Hsin-Chu, Taiwan

[21] Appl. No.: 09/240,110

[22] Filed: Jan. 29, 1999

[51] Int. Cl.[7] .................................................. G01N 9/24
[52] U.S. Cl. .................. 73/601; 73/620; 250/559.42; 356/237.1
[58] Field of Search ........................... 73/601, 620, 624; 250/341.4, 559.42, 559.14, 559.13; 356/237.1, 237.2

[56] References Cited

U.S. PATENT DOCUMENTS

| | | | |
|---|---|---|---|
| 4,011,748 | 3/1977 | Bono et al. | 73/601 |
| 4,741,212 | 5/1988 | Rehwald | 73/600 |
| 5,479,252 | 12/1995 | Worster et al. | 250/559.42 |
| 5,592,295 | 1/1997 | Stanton et al. | 356/237.2 |

*Primary Examiner*—John E. Chapman
*Attorney, Agent, or Firm*—Tung & Associates

[57] ABSTRACT

An apparatus for detecting defects in a wafer edge and a method for detecting are disclosed. In the apparatus, an ultrasonic detection unit is used to detect crazing or micro-cracks in a wafer edge, while a laser detection unit is used for detecting cracks in the wafer edge. The ultrasonic detection unit and the laser detection unit may be positioned in a detection module together with a wafer platform for holding and rotating a wafer positioned thereon. The detection module is placed in a mini-environment of clean room conditions which also include a robot transport device and a wafer storage cassette. The present invention novel apparatus is compact in size and can be moved to any location in a fab plant such that it is positioned adjacent to a process machine. The present invention novel apparatus can be used to detect crazing (or micro-cracks) and cracks that are present in an edge portion of a wafer which may be caused by external stresses during various processing steps such as polishing, cleaning and edge bead rinsing.

24 Claims, 5 Drawing Sheets

** # APPARATUS FOR DETECTING WAFER EDGE DEFECTS AND METHOD OF USING

FIELD OF THE INVENTION

The present invention generally relates to an apparatus and a method for detecting edge defects in a substrate and more particularly relates to an apparatus and a method for detecting in a silicon wafer edge defects such as crazing by an ultrasonic detection device and cracks by a continuous laser detection device.

BACKGROUND OF THE INVENTION

In the fabrication of electronic devices, semi-conducting silicon material in the form of wafers is most frequently used for forming electronic circuits in a miniature scale. In the processing of electronic wafers, an extremely clean and contaminant-free environment is normally used to ensure that defect-free circuits are formed on the surface of the wafer. Through the various processing steps, either a high vacuum, a high temperature, a hostile chemical environment or the combination thereof must be utilized as the environment for carrying out the processing steps. A high stress is frequently imposed on the wafer during such processing steps. After an electronic wafer is processed in a processing step, the wafer needs to be cleaned and prepared for the next step of process. The cleaning step for the wafer may involve a general cleaning in which a deionized water jet is sprayed on the entire surface of the wafer, or a specific cleaning step for the wafer edge to remove a photoresist coating or a spin-on-glass coating by an edge bead rinse process.

The edge bead rinse process is necessary for removing an edge bead of either a photoresist or a SOG material such that the wafer may be clamped in a future process by a clamp ring without producing particulate contaminants. In an edge bead rinse process, a high pressure water jet is used for impinging on an edge portion of the wafer so that the coating layer may be flushed away. A high stress is imposed on the wafer edge during the edge bead rinse process. The process therefore further contributes to the formation of crazing (frequently defined as micro-cracks) and cracks in a wafer edge. Both defects may present a serious problem for the electronic wafer and the IC circuits built thereupon. For instance, crazing may cause broken circuits in the IC chips, and may develop into cracks eventually if the specific area of the wafer is further stressed. The formation of cracks in a wafer edge also presents the problem that a whole section of the edge portion may be lost.

Traditionally, crack defects in a wafer edge is determined by visual examination under suitable lighting conditions by a process technician. The wafer may be positioned on a wafer platform which may be tilted to any suitable angle to minimize light reflection from the wafer surface which may lead to defects not being detected. The wafer platform may also be rotated at a suitable rotational speed to facilitate the visual examination. The findings of cracks in the wafer edge portion, even though can be performed in a visual examination, is a time consuming and unreliable process.

The detection of crazing or micro-cracks that has not yet developed into a full crack, is more difficult than the detection of cracks. Presently, there is no reliable method or apparatus can be used to perform such detection.

It is therefore an object of the present invention to provide an apparatus that detects crazing and cracks in a wafer edge without the shortcomings or drawbacks of the conventional apparatus.

It is another object of the present invention to provide an apparatus for determining crazing and cracks in a wafer edge that can be used to produce reliable results.

It is a further object of the present invention to provide an apparatus for detecting crazing and cracks that can be operated in an automated manner.

It is another further object of the present invention to provide an apparatus for detecting crazing and cracks in a wafer edge that utilizes an ultrasonic detection unit for detecting crazing.

It is still another object of the present invention to provide a method for detecting crazing and cracks wherein a laser detection unit is utilized to detect cracks.

It is yet another object of the present invention to provide a method for detecting crazing and cracks in a wafer edge by utilizing ultrasonic waves and laser irradiation.

It is still another further object of the present invention to provide a method for detecting crazing and cracks in a wafer edge that functions in a mini-clean room environment without contamination problems.

It is yet another further object of the present invention to provide a method for detecting crazing and cracks in a wafer edge by utilizing a continuous laser source for detecting cracks or missing edge portions in a wafer.

SUMMARY OF THE INVENTION

In accordance with the present invention, an apparatus and a method for detecting crazing and cracks in the edge of a semiconductor wafer are provided.

In a preferred embodiment, an apparatus for detecting defects on a wafer edge can be provided which includes an enclosure of a clean room environment for housing therein a robot transport arm, a wafer storage cassette and a detection module, the detection module may further include a wafer platform for holding and rotating a wafer positioned thereon, the wafer has an edge portion that contains at least one defect selected from the group consisting of crazing and cracks, an ultrasonic detection unit for emitting and receiving an ultrasonic wave reflected by crazing in the wafer edge, and a laser detection unit for emitting and receiving a laser irradiation interfered by cracks in the wafer edge.

The apparatus for detecting defects in a wafer edge may further include a process controller for controlling the test sequence, a visual inspection module for holding a wafer at a predetermined tilt angle for visual inspection. The ultrasonic detection unit may consist of an ultrasonic wave emitter and an ultrasonic wave receiver. The laser detection unit may consist of a laser emitter and a laser receiver.

In the apparatus, the enclosure may provide a "Class 1" clean room mini-environment. The wafer storage cassette may provide a SMIF interface. The laser detection unit may include a continuous laser emission source. The apparatus may further include registering means in the detection module for locating a center and a flat edge of the wafer for proper positioning of the wafer on the wafer platform.

In an alternate embodiment, a module for detecting defects on an edge of a substrate is provided which may include a platform for supporting and rotating a substrate positioned thereon, the substrate may have an edge portion containing at least one defect of crazing or crack, an ultrasonic detection unit for emitting and receiving an ultrasonic wave to and from the crazing in the edge portion of the substrate, and a laser detection unit for emitting and receiving a laser irradiation interfered by cracks in the edge portion of the substrate.

The module for detecting defects on an edge of a substrate may further include a process controller for processing data from the ultrasonic detection unit and the laser detection unit. The module may contain an ultrasonic detection unit of an ultrasonic wave emitter and receiver. The module may further include a laser detection unit consists of a laser emitter and a laser receiver. The module may further include a substrate storage cassette and a robot transporting device. The laser detection unit may include a continuous laser emission source.

The present invention is further directed to a method for detecting defects on a wafer edge which can be carried out by the operating steps of first providing a detecting module that includes a wafer platform for supporting and rotating a wafer, an ultrasonic detection unit and a laser detection unit, then positioning the detection module in an enclosure of a clean room environment, rotating the wafer on the wafer platform, emitting an ultrasonic wave toward an edge portion of the wafer and receiving a reflected wave from a crazing defect on the edge portion, emitting a laser irradiation towards an edge portion of the wafer and receiving a reflected radiation from a crack defect on the edge portion, and processing the reflected ultrasonic wave and the reflected laser irradiation by a process controller.

The method for detecting defects in a wafer edge may further include the step of controlling a test sequence by the process controller, or visually examining the wafer in a visual inspection module wherein the wafer may be presented in a tilted position. The method may further include the step of emitting a laser irradiation towards an edge portion of the wafer and receiving the irradiation in a receiver when an edge portion on the wafer is missing. The laser irradiation may be delivered in a continuous mode. The method may further include the step of evacuating the enclosure to a "Class 1" clean room condition, or the step of delivering a wafer from a wafer cassette. The method may further include the step of delivering a wafer from and to a wafer cassette prior to and after a defect test by a robot device, or the step of registering the wafer on the wafer platform by locating a center and a flat edge of the wafer for proper positioning.

BRIEF DESCRIPTION OF THE DRAWINGS

These and other objects, features and advantages of the present invention will become apparent from the following detailed description and the appended drawings in which.

DETAILED DESCRIPTION OF THE PREFERRED EMBODIMENT

The present invention discloses an apparatus for detecting defects in a wafer edge which includes an enclosure of a mini-environment of a clean room condition equipped with a robot transport arm, a wafer storage cassette and a detection module therein. The detection module further includes a wafer platform for holding and rotating a wafer, an ultrasonic detection unit for detecting crazing in the wafer edge, and a laser detection unit for detecting cracks in the wafer edge.

The present invention further discloses a method for detecting defects in a wafer edge by first providing a detecting module which includes a wafer platform, an ultrasonic detecting unit and a laser detection unit. The method is then carried out by positioning the detecting module in an enclosure of clean room environment, rotating the wafer on the wafer platform, emitting an ultrasonic wave toward an edge portion of the wafer and receiving a reflected wave from a crazing defect on the edge portion, emitting a laser irradiation toward an edge portion of the wafer and receiving a reflected irradiation from a crack defect on the edge portion, and then processing the reflected ultrasonic wave or the reflected laser irradiation by a process controller.

The present invention still further discloses a module which can be used for detecting defects on an edge portion of a substrate which includes a platform for supporting and rotating a substrate, an ultrasonic detection unit for detecting crazing in the edge portion of the substrate, and a laser detection unit for detecting cracks in the edge portion of the substrate.

In the fabrication of semiconductor wafers, defects in the edge portion of the wafer are frequently caused by external forces or stresses. For instance, defects of crazing and cracks can be formed after a polishing, a cleaning or an edge bead rinse process. While the crack defects can be easier discovered, the detection of crazing or micro-cracks that have not yet developed into cracks is very difficult. The present invention novel apparatus and method discloses the detection of microscopic defects such as crazing by an ultrasonic wave, i.e., by bouncing off an ultrasonic wave on the crazing defect and detecting a reflected wave as an indication of the defect. A laser detection unit is used for detecting larger defects such as cracks or missing portions on the wafer edge. The ultrasonic detection unit is therefore utilized for detecting invisible defects, while the laser detection unit is utilized for detecting visible defects.

Figure 1:
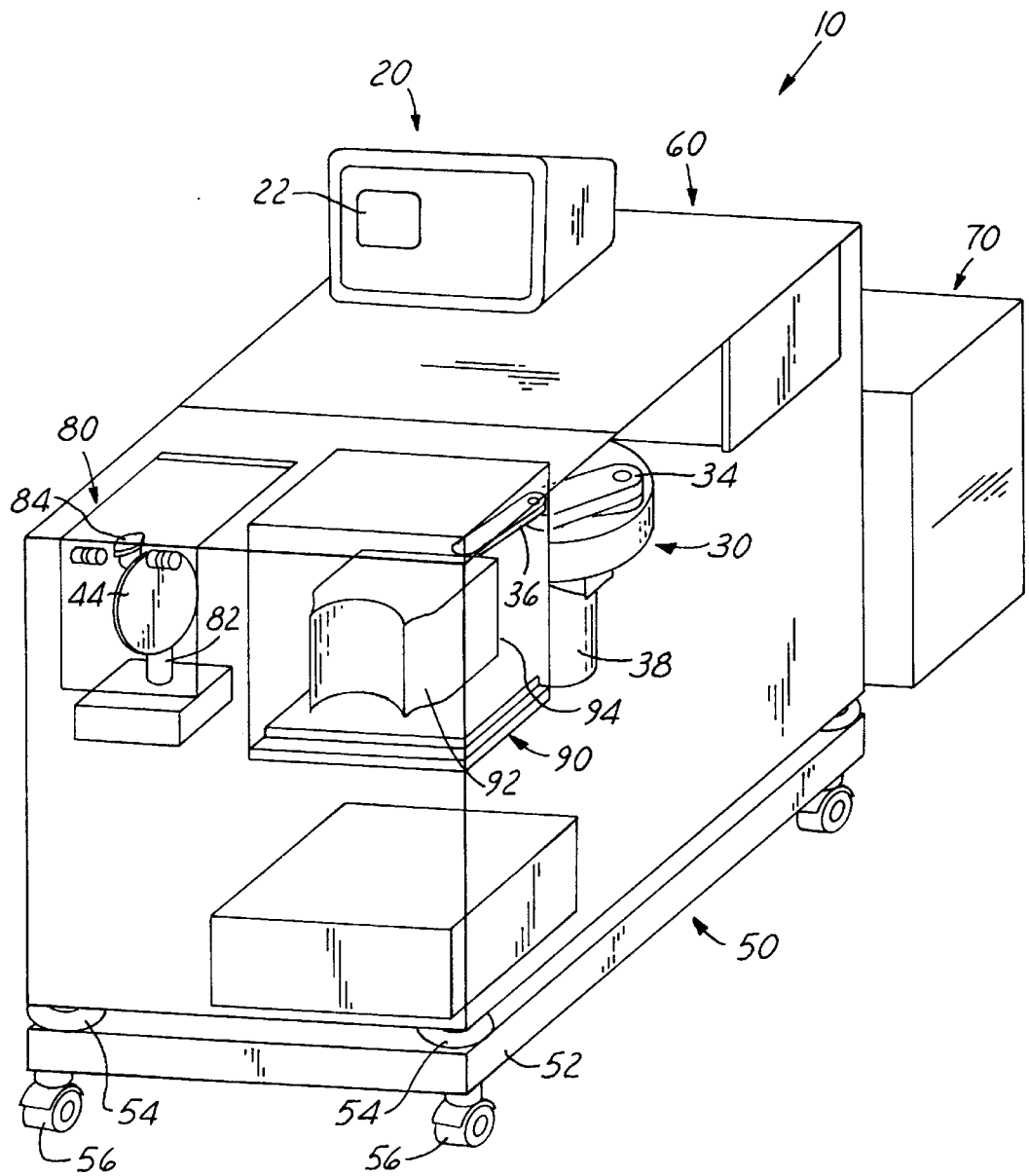
FIG. 1 is a perspective, partially exploded view of the present invention apparatus.

Referring now to FIG. 1, wherein a present invention novel apparatus 10 is shown. The apparatus 10 consists of the following major components: a process controller 20, a robot transfer unit 30, a positioning/detection module 40, a base/cushion anti-vibration module 50, a mini-clean room enclosure 60, a support module 70 and a visual inspection module 80. The physical size of the main frame, which includes the process controller 20, the robot transfer device 30, the base/cushion anti-vibration module 50, the mini-clean room enclosure 60 and the visual inspection module 80 is approximately 120 cm×80 cm×70 cm (L×W×H). The physical dimension of the support module 70 is approximately 50 cm×80 cm×50 cm (L×W×H).

The process controller 20 can be a process control microprocessor which is commonly available for monitoring and controlling the detecting steps of the present invention apparatus 10. A suitable memory capacity should be provided to ensure the operating speed of the processor 20 is adequate for the sensing and determination of defects. The process controller 20 may further include a display unit 22 which is used to display defects found by either the ultrasonic detection unit or the laser detection unit.

Figure 2:
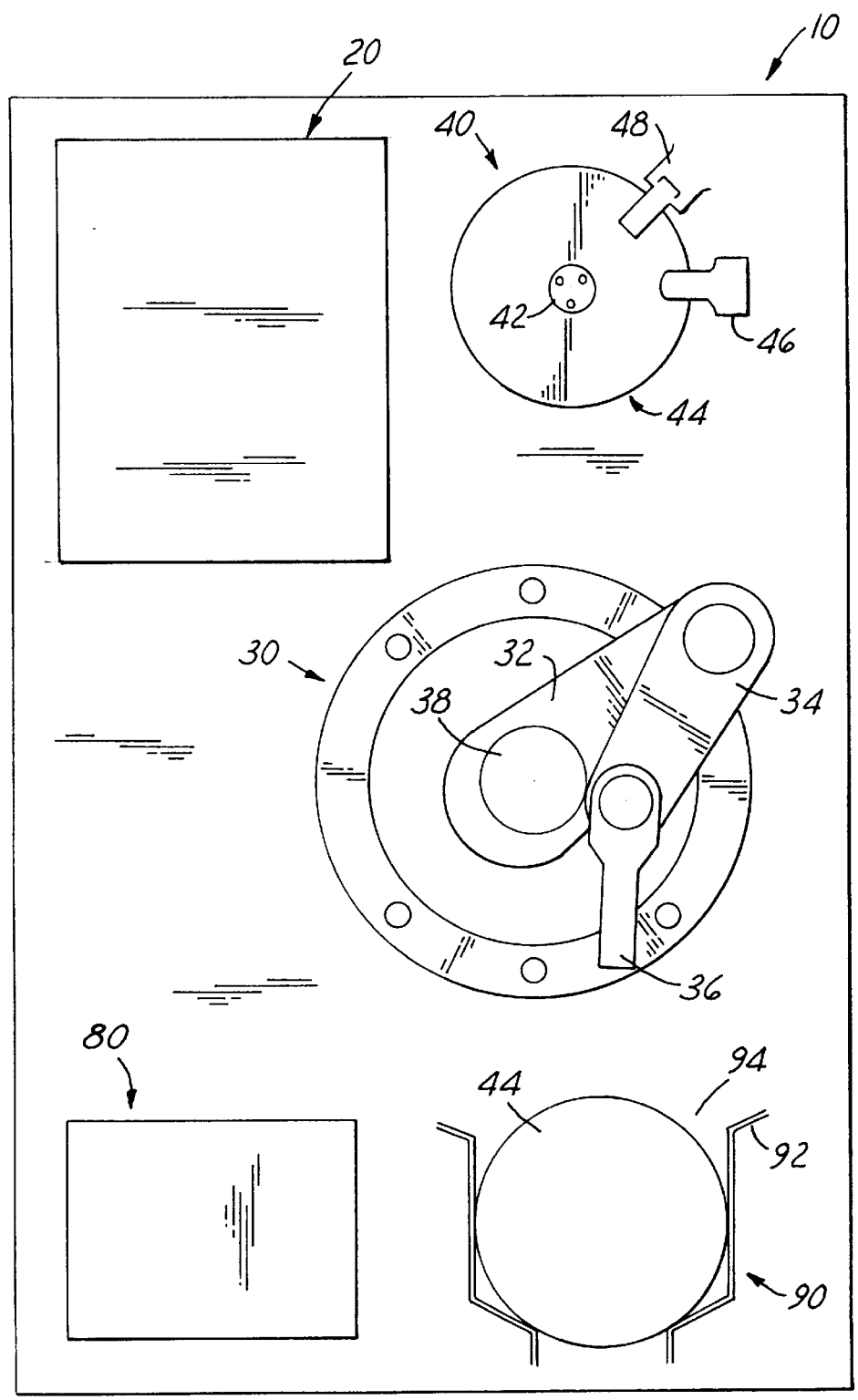
FIG. 2 is a plane view of the present invention apparatus.

The second major component of the present invention novel apparatus 10 is the robot transport device 30 which includes a robot transfer arm 32, 34 and a wafer blade 36, shown in FIG. 2. The robot transport device 30 further include an elevator 38 for moving the arms 32, 34 in an upward or in a downward direction for loading and unloading wafers into or out of the wafer cassette 92 situated in a SMIF interface module 90. The wafers (not shown) are loaded or unloaded through an open back 94 of the cassette 92. The wafer blade 36 carries a wafer (not shown) from the cassette 92 for transporting it into the detection module 40 and placing it on a wafer platform 42.

In the plane view shown in FIG. 2, a wafer 44 is positioned on a wafer platform 42 (FIG. 2) and then rotated at a suitably rotational speed for detection by an ultrasonic detection unit 46 and a laser detection unit 48. A suitable rotational speed for wafer 44 may be any speed lower than 100 RPM. Also shown in FIG. 2 are the wafers 44 positioned in the wafer cassette 92 and the open back 94 of the wafer cassette 92.

The visual inspection module 80, shown in FIGS. 1 and 2, is constructed by a rotatable, tiltable wafer stage 82 which rotates or tilts a wafer 44 positioned thereon for visual inspection. A suitable lighting fixture 84 is used to sufficiently illuminate the top surface of the wafer 44 for visual inspection by a process technician. It should be noted that the visual inspection step is optional since the automated detection module 40 is normally adequate in detecting all types of edge defects on the wafer.

The robot transport device 30 is capable of moving in x, y and z directions such that it is capable of picking up and delivering a wafer from any position. The SMIF interface apparatus 90 enables the wafers 44 contained in the wafer cassette 92 to be transported in an extremely clean environment, i.e., the mini environment 60 can be kept at a "Class 1" clean room condition.

Figure 4A:
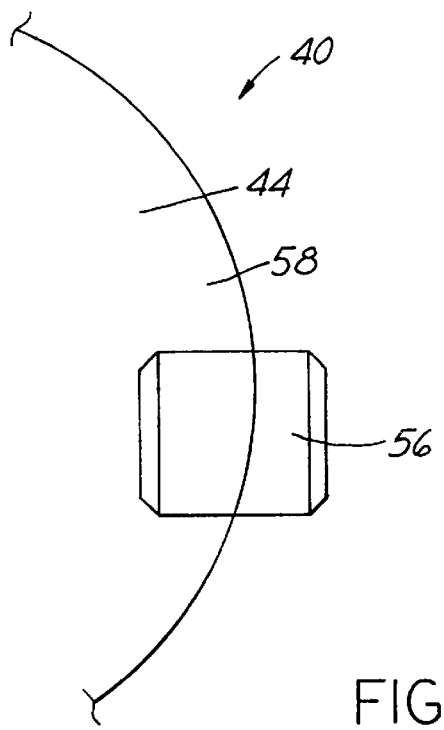
FIG. 4A is a top view showing the placement of the ultrasonic detection unit in relationship to a wafer.
Figure 4B:
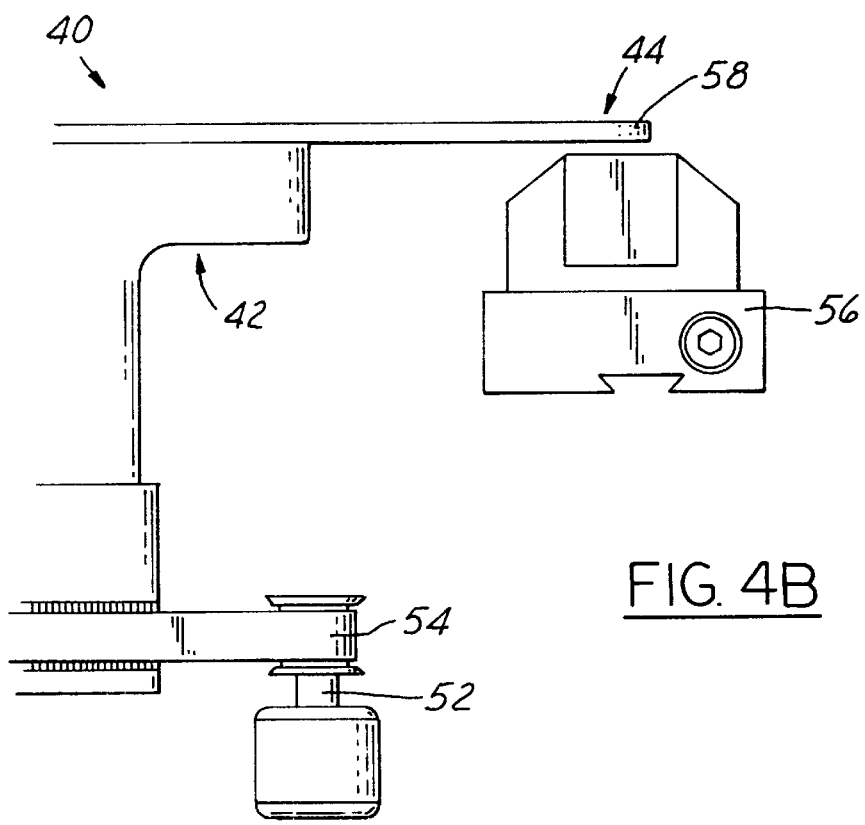
FIG. 4B is a side view showing the position of an ultrasonic detection unit in relation to a wafer.

The most important part of the present invention apparatus is the positioning/detection module 40 shown in FIGS. 1, 2, and in more detail in FIGS. 4A~5B. The functions accomplished by the positioning/detecting module 40 include the registering or positioning of a wafer 44 on the wafer pedestal 42 as the first step in the defect detection process. A center of the wafer 44 and the flat side (or the notch) of the wafer 44 are first detected for the proper registering of the wafer 44 on the platform 42. The wafer 44 is then rotated by the wafer platform 42 by motor 52 through a timing belt 54. An ultrasonic emitter 56 is positioned facing upwardly toward an edge 58 of the wafer 44. An ultrasonic receiver (not shown) then receives reflected ultrasonic waves from the surface defects, i.e., crazing or micro-cracks which are present on the wafer edge 58. The signals received by the ultrasonic receiver is then sent to a process controller 20 for data processing and for displaying the results of detection in the display unit 22. A detailed arrangement of the ultrasonic detection unit, or of the ultrasonic emitter 56 and the wafer 44 are shown in FIGS. 4A and 4B. FIG. 4A is a plane view showing the wafer 44 in relation to the ultrasonic emitter 56.

Figure 5A:
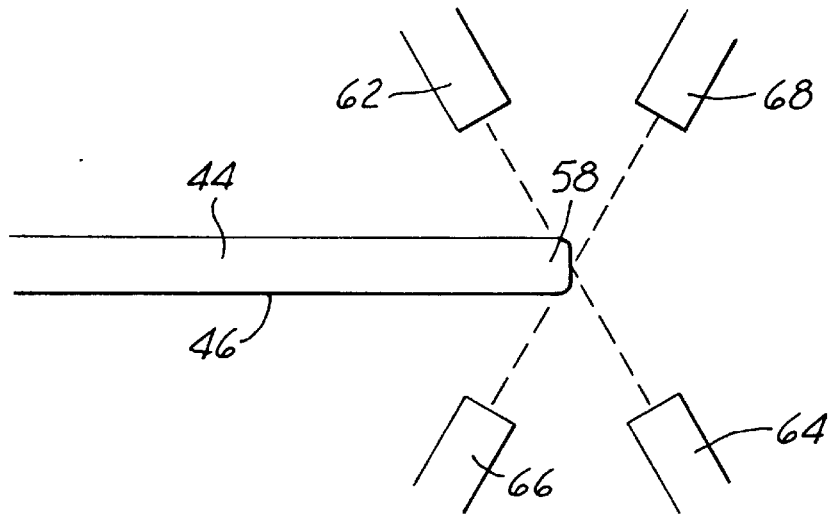
FIG. 5A is a side view of the present invention laser detection device in relation to a wafer that does not have edge cracks.
Figure 5B:
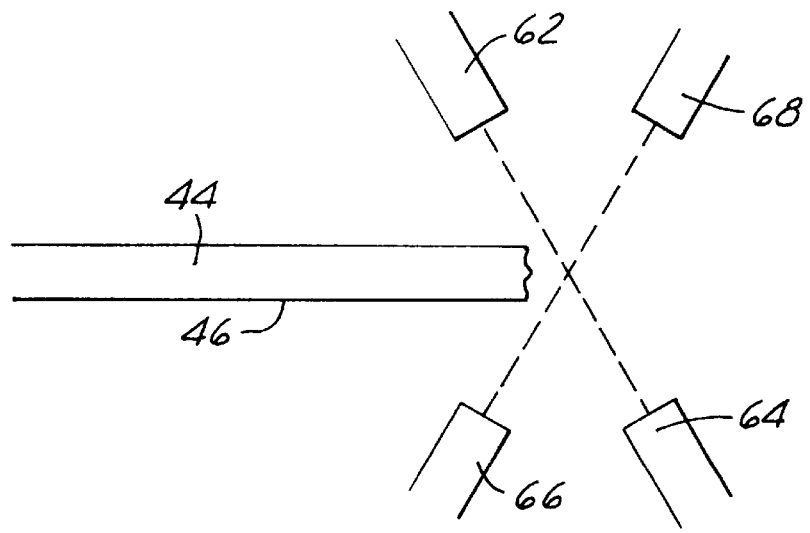
FIG. 5B is a side view of the present invention laser detection unit in relation to a wafer that has a crack in an edge portion.

A laser detector which includes a laser emitter 62 and a laser receiver 64 positioned in relation to a wafer 44 is shown in FIGS. 5A and 5B. It should be noted that, in FIG. 5B, the edge portion 58 broke off the wafer 44 and is missing. Also shown in FIGS. 5A and 5B is a second set of laser emitter 66 and laser receiver 68. The emitter 66 and receiver 68 provide further capability of the laser detection unit for detecting smaller cracks that may appear only on the bottom side 46 of the wafer 44. A continuous laser is normally used as the laser emitter 62, 66 such that larger defects such as cracks or missing edges can be detected.

The present invention novel apparatus is supported by a base plate/cushion module 50 which consists of a base plate 52 and a set of air cushions 54. The base plate 52 is further supported by a set of casters 56 which can be rolled easily on a flat surface for mobility of the apparatus 10. The air cushions 54 support the mini-environment 60 such that it is isolated from all vibrations. The support module 70 contains major elements for supplying a vacuum to the robot transport system 30 and air pressure to the air cushions 54 placed under the mini-environment 60.

Figure 3:
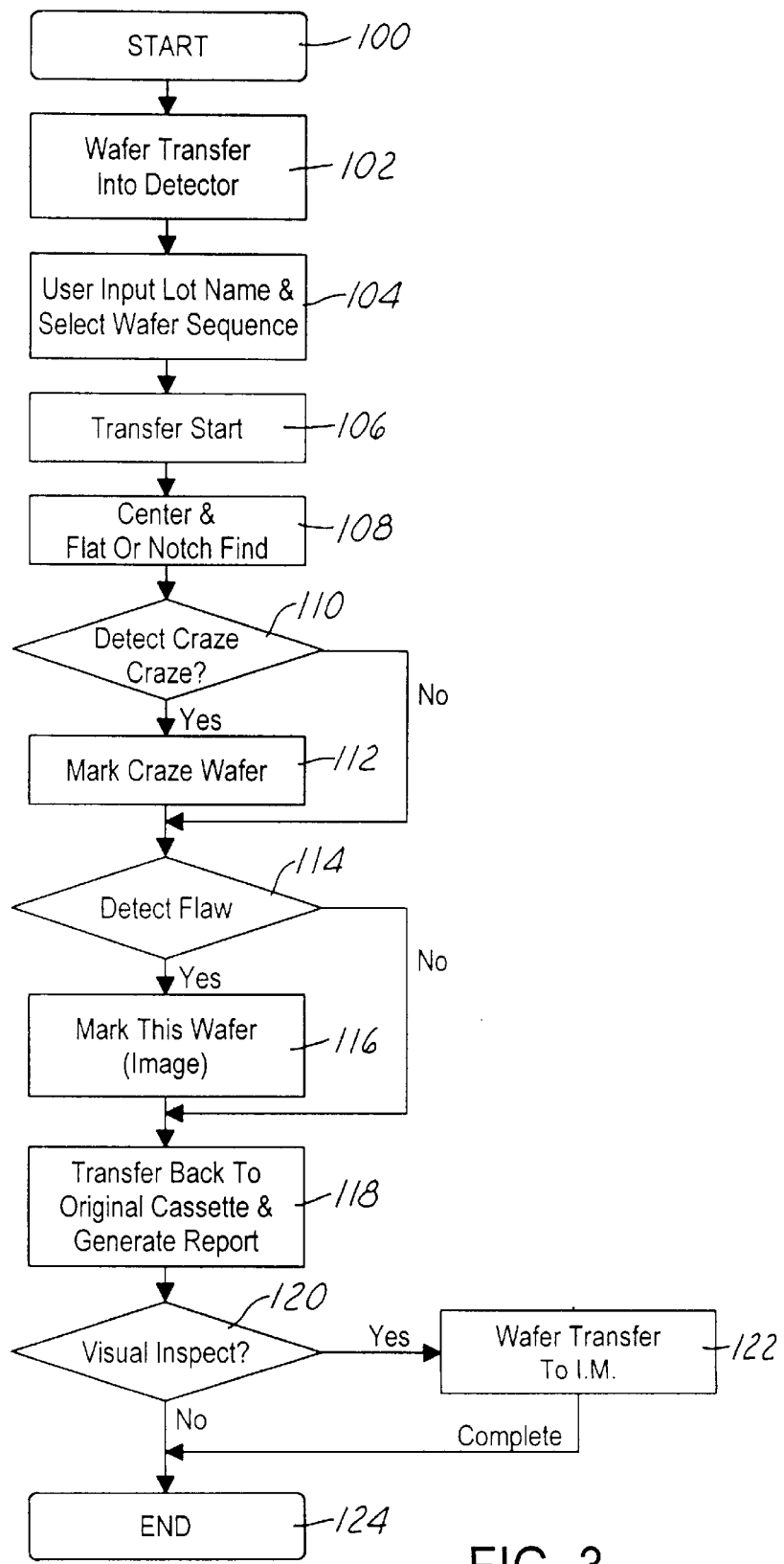
FIG. 3 is a process flow chart for the present invention method of detecting crazing and cracks.

The mini-environment 60 is capable of supplying a "Class 1" clean room environment inside the enclosure by generating a downstream flow for preventing contamination of the wafer by particles. The present invention novel detection apparatus 10 can be advantageously moved around on a factory floor for placement adjacent to a wafer processing station. The operation of the present invention novel apparatus 10 is shown in FIG. 3. At the start 100 of the process, a wafer is first transferred into the mini-environment 60 in step 102 such that a wafer cassette is placed in the SMIF interface unit. As shown by step 104, end user then inputs the lot name and number into the process controller and selects a wafer test sequence. In the next step 106, a wafer transfer from the wafer cassette to the detection module is started by the operation of the robot transport device. First, as shown by step 108, the center of the wafer and the flat or the notch on the wafer is found before the wafer is positioned on a wafer platform in the detection module. At the start of the detection process 110, an ultrasonic detection unit first operates to detect crazing or micro-cracks. If crazing or micro-cracks are found, the wafer is marked at the proper location as shown in step 112. If no crazing or micro-cracks are found, the next step of the detection process 114 is carried out to detect cracks. When cracks are found on the wafer edge, the wafer is marked at the proper location in step 116. In the event that no cracks are discovered, the wafer is transported back to the wafer cassette and a report is generated on the test sequence and result. This is shown in step 118. A decision is then made regarding whether a visual inspection of the wafer is necessary in step 120. If it is decided that a visual inspection is needed, the wafer is transported to the visual inspection module in step 122. The process ends at step 124. If it was determined that visual inspection is not necessary, the detection process also ends at step 124.

The present invention novel apparatus and method for detecting crazing and cracks in wafer edge have therefore been amply demonstrated in the above descriptions and in the appended drawing of FIGS. 1~5B.

While the present invention has been described in an illustrative manner, it should be understood that the terminology used is intended to be in a nature of words of description rather than of limitation.

Furthermore, while the present invention has been described in terms of a preferred embodiment, it is to be appreciated that those skilled in the art will readily apply these teachings to other possible variations of the inventions.

The embodiment of the invention in which an exclusive property or privilege is claimed are defined as follows:

What is claimed is:

1. An apparatus for detecting defects in a wafer edge comprising:
   an enclosure of a clean room environment for housing therein a robot transport arm, a wafer storage cassette and a detection module, said detection module further comprises:

a wafer platform for holding and rotating a wafer positioned thereon, said wafer having an edge portion containing at least one defect selected from the group consisting of crazing and cracks, an ultrasonic detection unit for emitting and receiving an ultrasonic wave reflected by a crazing in said wafer edge, and a laser detection unit for emitting and receiving a laser irradiation interfered by cracks in said wafer edge.

2. An apparatus for detecting defects in a wafer edge according to claim 1 further comprising a process controller for controlling a test sequence.

3. An apparatus for detecting defects in a wafer edge according to claim 1 further comprising a visual inspection module for holding a wafer at a predetermined tilt angle for visual inspection.

4. An apparatus for detecting defects in a wafer edge according to claim 1, wherein said ultrasonic detection unit consists of an ultrasonic wave emitter and an ultrasonic wave receiver.

5. An apparatus for detecting defects in a wafer edge according to claim 1, wherein said laser detection unit consists of a laser emitter and a laser receiver.

6. An apparatus for detecting defects in a wafer edge according to claim 1, wherein said enclosure provides a "Class 1" clean room environment.

7. An apparatus for detecting defects in a wafer edge according to claim 1, wherein said wafer storage cassette provides a SMIF interface.

8. An apparatus for detecting defects in a wafer edge according to claim 1, wherein said laser detection unit comprises a continuous laser emission source.

9. An apparatus for detecting defects in a wafer edge according to claim 1 further comprising registering means in said detection module for locating a center and a flat edge of said wafer for proper positioning of the wafer on said wafer platform.

10. A module for detecting defects in an edge of a substrate comprising:

a platform for supporting and rotating a substrate positioned thereon, said substrate having an edge portion containing at least one defect of crazing or crack, an ultrasonic detection unit for emitting and receiving an ultrasonic wave to and from said crazing in said edge portion of the substrate, and a laser detection unit for emitting and receiving a laser irradiation interfered by cracks in said edge portion of the substrate.

11. A module for detecting defects in an edge of a substrate according to claim 10 further comprising a process controller for processing data from said ultrasonic detection unit and said laser detection unit.

12. A module for detecting defects in an edge of a substrate according to claim 10, wherein said ultrasonic detection unit consists of an ultrasonic wave emitter and an ultrasonic wave receiver.

13. A module for detecting defects in an edge of a substrate according to claim 10, wherein said laser detection unit consists of a laser emitter and a laser receiver.

14. A module for detecting defects in an edge of a substrate according to claim 10 further comprising a substrate storage cassette and a robot delivery device.

15. A module for detecting defects in an edge of a substrate according to claim 10, wherein said laser detection unit comprises a continuous laser emission source.

16. A method for detecting defects in a wafer edge comprising the steps of:

providing a detection module which comprises a wafer platform for supporting and rotating a wafer, an ultrasonic detection unit and a laser detection unit, positioning said detection module in an enclosure of a clean room environment, rotating said wafer on said wafer platform, emitting an ultrasonic wave toward an edge portion of said wafer and receiving a reflected wave from a crazing defect in said edge portion, emitting a laser irradiation toward an edge portion of said wafer and receiving a reflected irradiation from a crack defect on said edge portion, and processing said reflected ultrasonic wave and said reflected laser irradiation by a process controller.

17. A method for detecting defects in a wafer edge according to claim 16 further comprising the step of controlling a test sequence by said process controller.

18. A method for detecting defects in a wafer edge according to claim 16 further comprising the step of visually examining said wafer in a visual inspection module wherein said wafer is held in a tilted position.

19. A method for detecting defects in a wafer edge according to claim 16 further comprising the step of emitting a laser irradiation toward an edge portion of the wafer and receiving said irradiation in a receiver when an edge portion on said wafer is missing.

20. A method for detecting defects in a wafer edge according to claim 16, wherein said laser irradiation is delivered in a continuous mode.

21. A method for detecting defects in a wafer edge according to claim 16 further comprising the step of evacuating said enclosure to a "Class 1" clean room condition.

22. A method for detecting defects in a wafer edge according to claim 16 further comprising the step of delivering a wafer from a wafer cassette.

23. A method for detecting defects in a wafer edge according to claim 16 further comprising the step of delivering a wafer from and to a wafer cassette prior to and after a defect test by a robot device.

24. A method for detecting defects in a wafer edge according to claim 16 further comprising the step of registering said wafer on said wafer platform by locating a center and a flat edge of said wafer for proper positioning.

* * * * *